United States Patent [19]

Barcelo et al.

[11] Patent Number: 4,725,680

[45] Date of Patent: Feb. 16, 1988

[54] PROCESS FOR THE PREPARATION OF CARBAMATES, THIOCARBAMATES AND UREAS

[75] Inventors: Gérard Barcelo, Sainte Genevieve des Bois; Jean-Pierre Senet, La Chapelle la Reine; Gérard Sennyey, Gif sur Yvette, all of France

[73] Assignee: Societe Nationale des Poudres et Explosifs, Paris, France

[21] Appl. No.: 701,380

[22] Filed: Feb. 14, 1985

[30] Foreign Application Priority Data

Feb. 16, 1984 [FR] France ............................... 84 02327

[51] Int. Cl.$^4$ ............................................ C07D 223/04
[52] U.S. Cl. ....................................... 540/608; 560/24; 560/32; 560/132; 560/157; 560/160; 560/163; 560/165; 558/232; 564/61; 564/63; 564/255; 564/483; 548/341; 548/533; 548/531; 549/462; 549/490; 549/496; 546/210; 546/226; 546/245; 544/172
[58] Field of Search ............... 548/531, 533, 341; 560/157, 24, 32, 160, 163, 165, 132; 564/61, 63, 255, 483; 549/496, 462, 490; 546/245, 226, 210; 544/172; 540/608; 558/232

[56] References Cited

U.S. PATENT DOCUMENTS 3,763,217 10/1973 Brill ....................................... 560/24

FOREIGN PATENT DOCUMENTS 2201870 6/1974 France .

OTHER PUBLICATIONS

Patai, ed., *The Chemistry of Carboxylic Acids and Esters,* Interscience (1969), pp. 576-579.

*Primary Examiner*—Donald G. Daus
*Assistant Examiner*—William A. Teoli, Jr.
*Attorney, Agent, or Firm*—Bucknam and Archer

[57] ABSTRACT

The invention relates to a process for preparing carbamic acid derivatives of formula:

$$\begin{array}{c} R^1 \\ \phantom{R^1}\diagdown \\ \phantom{R^1R^1}N-C-Y \\ \phantom{R^1}\diagup \phantom{N}\| \\ R^2 \phantom{\diagup N}O \end{array}$$

in which $R^1$ or $R^2$ denotes a hydrogen atom or a substituted or unsubstituted, saturated or unsaturated aliphatic, cycloaliphatic or heterocyclic radical, or $R^1$ and $R^2$ together form a ring, and Y denotes OR, SR, $$-N\diagup^{R^3}_{\diagdown R^4} \text{, or } O-N=C\diagup^{R^6}_{\diagdown R^7},$$

groups, R being a substituted or unsubstituted, saturated or unsaturated aliphatic or cycloaliphatic radical, or a substituted or unsubstituted aromatic radical, $R^3$ and $R^4$ denote a hydrogen atom or an aliphatic, cycloaliphatic, araliphatic, aromatic or heterocyclic radical or together form a ring, and $R^6$ and $R^7$ denote a saturated or unsaturated, substituted or unsubstituted aliphatic or cycloaliphatic radical, a hydrogen atom, an alkylthio radical or an alkyloxy radical.

According to the process, a compound of formula $$\text{NH}\diagup^{R^1}_{\diagdown R^2}$$

is reacted with an α-halogenated derivative of formula $$\begin{array}{c} R^5-CH-O-C-Y \\ \phantom{R^5-CH}| \phantom{O-}\| \\ \phantom{R^5-CH}X \phantom{O-}O \end{array}$$

at a temperature of −5° to 150° C. in the presence of an acceptor for hydrohalic acid.

The carbamates, thiocarbamates or ureas obtained are very useful, especially as pesticides.

14 Claims, No Drawings

PROCESS FOR THE PREPARATION OF CARBAMATES, THIOCARBAMATES AND UREAS

The invention relates to a new process for preparing carbamic acid derivatives. More specifically, it relates to a process for preparing derivatives of formula:

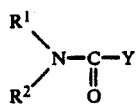

in which Y denotes an alcohol, mercaptan or amine residue, which derivatives are consequently carbamates, thiocarbamates or ureas.

The processes most commonly used for preparing these compounds are, for example, for carbamates and thiocarbamates, the reaction of a chloroformate or thiochloroformate with an amine, as described in the article in Chemical Review, 1964, 64, pages 656-663, or that of a carbamyl chloride or an isocyanate with an alcohol, phenol or mercaptan (Grignard: Traité de Chimie Organique, volume XIV, page 20-31).

As regards ureas, these are most frequently obtained by reacting an isocyanate or a carbamyl chloride with an amine. When they are symmetrical they can also be prepared by phosgene treatment of an amine (Grignard: volume XIV, pages 85, 30).

However, these various processes do not always enable the desired compounds to be prepared, or they are sometimes difficult to implement.

Some starting materials are:

unstable, as is the case with a number of chloroformates such as, for example, furfuryl, tert-butyl and p-methoxybenzyl chloroformates;

toxic, such as isocyanates, phosgene and especially light carbamyl chlorides which are carcinogenic, or pollutant, such as light thiochloroformates.

Research has been carried out to find new routes.

A few compounds have been prepared by reacting dimethyl carbonate or ethylphenyl carbonate with aniline in the presence of a catalyst such as uranyl nitrate, but the yields are very low, the mixture has to be heated to a high temperature (100°; U.S. Pat. No. 3,763,217), and by-products are obtained in substantial quantities.

Diphenyl carbonate does not react with amines to give a carbamate except in the presence of a catalyst such as 2-hydroxypyridine [Noboru Yamazaki and Todao Igudi, Fukuji Higashi, Journal of Polymer Science, vol. 17, pages 835-841 (1979)].

Other carbamation agents have been proposed such as:

azides. Synthesis of these is performed in several stages and is awkward. They can decompose explosively, like BOC azide (Angew, Chem., Ind. Ed. Engl. 16 1977 no. 2), several trials have been performed with very special carbonates such as mixed p-nitrophenyl carbonates. The by-products obtained are difficult to remove, bicarbonates. Synthesis of these is very awkward and expensive. This is particularly the case with tert-butyl bicarbonate. Moreover, a protective residue is lost, fluoroformates, the preparation of these is difficult however because it demands the use of non-commercial starting materials which are awkward to handle, such as ClCOF or BrCOF.

The reaction of some carbamates with amines has been studied. The urea is only obtained after heating to high temperatures of the order of 150° to 230° and on condition that a catalyst is used (Phillip Adams and Franck A. Baron, Chemical Review, 1965, page 574).

In these various processes, an alcohol or a phenol is always formed which is very often difficult to remove, and the reaction is reversible.

In some cases, it is absolutely impossible to prepare the urea. Thus, when ethyl N-imidazolecarbamate is reacted with ethylamine, ethyl N-ethylcarbamate and imidazole are obtained, and not the urea.

This brief survey shows the limits of the conventional processes and the meagre results obtained by the new routes.

It was hence desirable that a general process should be available for preparing carbamic acid derivatives which was easier to implement both as regards the use of less dangerous starting compounds and also as regards the working conditions and the removal of by-products.

The process according to the present invention is applicable to the preparation of a large number of carbamic acid derivatives, and is especially suitable when the other routes leading to these derivatives are unsuitable.

The invention relates to a process for preparing carbamic acid derivatives of general formula:

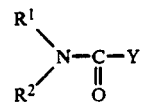

in which $R^1$ and $R^2$, which may be identical or different, denote:

a hydrogen atom, a substituted or unsubstituted, saturated or unsaturated, linear or branched aliphatic or araliphatic radical, a substituted or unsubstituted, saturated or unsaturated cycloaliphatic radical, a substituted or unsubstituted, saturated or unsaturated heterocyclic radical, or together form with the nitrogen atom to which they are bound a saturated or unsaturated, substituted or unsubstituted ring which can contain one or more heteroatoms and which can form part of a ring system. Y denotes OR, SR,

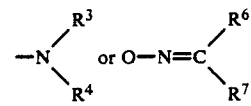

groups in which R denotes a substituted or unsubstituted, saturated or unsaturated, linear branched aliphatic or araliphatic radical, a substituted or unsubstituted, saturated or unsaturated cycloaliphatic residue, or a substituted or unsubstituted aromatic residue, $R^3$ and $R^4$, which may be identical or different, denote a hydrogen atom, a substituted or unsubstituted, saturated or unsaturated aliphatic, araliphatic, cycloaliphatic or heterocyclic radical, or a substituted or unsubstituted aromatic radical, or together form with the nitrogen atom to which they are bound a saturated or unsaturated, substituted or unsubstituted heterocycle which can contain 1 or more other hetero atoms, and $R^6$ and $R^7$, which may be identical or different, denote a saturated or unsaturated, substituted or unsubstituted, linear or branched aliphatic or cycloaliphatic radical, or denote, but not at the same time, a hydrogen atom, an alkylthio radical or an alkyloxy radical.

This process consists in reacting, in the presence of an acceptor for hydrohalic acid at a temperature of between −5° and 150°, a hydrogen-containing amino compound of formula:

$$NH\begin{matrix}R^1\\R^2\end{matrix}$$

with an α-halogenated derivative of carbonic acid of formula:

$$R^5-\underset{X}{CH}-O-\underset{O}{\overset{\parallel}{C}}-Y$$

in which $R^1$, $R^2$ and Y have the above significance, X denotes a fluorine, chlorine or bromine atom and $R^5$ denotes a hydrogen atom, a substituted or unsubstituted, saturated or unsaturated, aliphatic, araliphatic or cycloaliphatic residue or a substituted or unsubstituted aromatic residue.

The reaction can be performed in the presence or absence of a solvent.

The reaction scheme can be written as follows:

$$\begin{matrix}R^1\\R^2\end{matrix}NH + R^5-\underset{X}{CH}-O-\underset{O}{\overset{\parallel}{C}}-Y \longrightarrow$$

$$\begin{matrix}R^1\\R^2\end{matrix}N-\underset{O}{\overset{\parallel}{C}}-Y + R^5-CHO + HX$$

It is observed that, surprisingly, HX is eliminated but this is not accompanied by attachment of the amine residue $$\begin{matrix}R^1\\R^2\end{matrix}N-$$

to the carbon which bears the halogen to form:

$$R^5-CH-O-\underset{O}{\overset{\parallel}{C}}-Y$$
$$\quad\quad\underset{R^2}{\overset{R^1}{\diagdown N \diagup}}$$

as would normally be expected, and as is the case, for example, in the reaction of an α-chlorinated carbonate with an acid:

$$R'-\underset{Cl}{CH}-O-\underset{O}{\overset{\parallel}{C}}-O-R'' + R'''COOH\longrightarrow$$

$$R'CH-O-\underset{O}{\overset{\parallel}{C}}-O-R''$$
$$\quad\quad | $$
$$\quad\quad O-\underset{O}{\overset{\parallel}{C}}-R'''$$

(ASTRA—Patent FR No. 2,201,870)

In contrast, according to our process, there is cleavage of the α-halogenated derivative, attachment of the $$Y-\underset{O}{\overset{\parallel}{C}}-$$

group to the residue of the amino compound and formation of the aldehyde $R^5CHO$.

As starting hydrogen-containing amino compound of formula:

$$\begin{matrix}R^1\\R^2\end{matrix}NH,$$

ammonia and the majority of known primary or secondary amines can be used.

When $R^1$ or $R^2$ denotes an aliphatic radical, it preferably contains from 1 to 20 carbon atoms. $R^1$ and $R^2$ can also signify a cycloaliphatic or araliphatic radical which can contain up to 50 carbon atoms, for example a benzyl radical, or together they can form a heterocycle, for example a piperidino, morpholino or imidazolyl ring.

The substituents of $R^1$ and $R^2$ can be various groups such as hydrocarbon groups or acid, alcohol, ester, ether, mercapto or amino functional groups.

As useful amines, there may be mentioned methylamine, diethylamine, di-n-butylamine, isobutylamine, n-octylamine, ethanolamine, benzylamine, N-methyl-N-benzylamine, piperidine, imidazole, hexamethyleneimine, morpholine and diethanolamine.

The natural or synthetic, optically active or inactive or racemic amino acids used in peptide synthesis are also very suitable.

There may be mentioned, for example, L-phenylalanine, L-proline, glycine, L-tyrosine, L-serine, L-aspartic acid, proline, ethyl glycinate and phenylglycine.

The second starting compound used can be an α-halogenated carbonate, thiocarbonate or carbamate. It is preferably α-chlorinated.

Preparation of this compound may be accomplished by various known processes, for example, for chlorinated derivatives, by reacting an α-chlorinated chloroformate of formula:

$$R^5-\underset{Cl}{CH}-O-\underset{O}{\overset{\parallel}{C}}-Cl$$

with a hydroxylated compound or a mercaptan, as described in the article by M. Matzner, R. Kurkjy and R. J. Cotter [Chem. Rev. 64, pages 651–654 (1964)], or with an amine, by the process described in European patent application Nos. 45,234 or 83/401766.7.

α-Chlorinated chloroformates are themselves prepared very simply by the process of phosgene treatment of aldehydes claimed in European patent application No. 40,153.

The radical $R^5$ is preferably a light radical such as an aliphatic radical consisting of 1 to 4 carbon atoms, which can be substituted, preferably with halogen atoms and especially chlorine atoms. Methyl and trichloromethyl radicals are especially highly valued.

The radical R of the carbonate or thiocarbonate is very variable. This can be an aliphatic radical preferably containing from 1 to 12 carbon atoms, such as a methyl, ethyl or tert-butyl radical, which can be substituted, for example, with a heterocyclic radical such as furyl, an araliphatic radical, for example benzyl, a substituted or unsubstituted aromatic nucleus which may or may not form part of a ring system, such as phenyl or 2,3-dihydro-2,2-dimethyl-7-benzofuranyl.

The radical R, whichever its significance, can be substituted with one or more groups

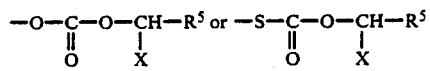

It is, in particular when the starting amine is an amino acid, one of the groups commonly used in peptide synthesis for protecting the amino group, such as tert-butyl, benzyl, para-nitrobenzyl, 9-fluorenylmethyl, 2,2,2-trichloroethyl, trimethylsilylethyl or furfuryl. α-Chlorinated and tert-butyl carbonates are partiularly highly valued in this case.

$R^3$ and $R^4$ present in the starting α-chlorinated carbamate denote, for example, a hydrogen atom or a methyl radical, or form together and with the nitrogen atom to which they are attached an imidazolyl ring. Thus, α-chloroethoxycarbonylimidazole and 1,2,2,2-tetrachloroethyl N-methylcarbamate are especially highly valued.

$R^6$ and $R^7$ denote, in particular, a hydrogen atom, a methylthio radical, a $C_1$ to $C_{12}$ aliphatic radical or a cycloaliphatic radical which can contain 30 carbon atoms. The substituents of $R^6$ and $R^7$ can be hydrocarbon radicals or groups containing hetero atoms, especially sulphur.

Since a release of halogen hydracid HX takes place during the reaction, the presence of an acceptor for acid is necessary for the removal of this acid.

The acceptor for acid can be an organic or inorganic base.

Among the preferred bases, there may be mentioned sodium hydroxide or potassium hydroxide, sodium carbonate or bicarbonate or potassium carbonate or bicarbonate, magnesium oxide, and sodium sulphite, which are generally used in the form of aqueous solutions, tertiary amines such as triethylamine, pyridine or N,N-dimethylaniline, and the starting amine itself of formula

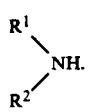

The amount of basic substance introduced into the medium should be sufficient to neutralise all the acid released. A slight excess relative to the stoichiometric quantity is preferably used.

The reaction according to the invention is preferably performed in solvent medium. One or more solvents are generally used which are inert towards the reagents. They are preferably chosen from chlorinated aliphatic solvents, such as dichloromethane or 1,2-dichloroethane, cyclic or acyclic ethers, for example tetrahydrofuran or dioxane, acetone, pyridine, acetonitrile, dimethylformamide or alcohols such as ethanol or tert-butanol. The reaction medium can contain a certain amount of water, necessary, for example, for the dissolution of inorganic bases.

The reaction temperature depends on the nature of the solvent and the reactivity of the starting compounds. It is between $-5°$ and $150°$ C. It is most frequently between $0°$ and $30°$ C. for the reaction of carbonates and thiocarbonates with amines, and between $30°$ and $100°$ C. for the reaction of carbamates.

The starting compounds are generally used in stoichiometric amounts. It is preferable to use a slight excess of one of the two reagents.

When the starting amine is used as acceptor for acid, at least two equivalents of amine are used per

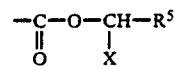

group to be converted.

The order in which the reagents are introduced is not a basic feature of the invention. However, when the amine is primary and is also used as acceptor base for acid, it is preferable to introduce it after the other starting compound.

The process of the invention enables many compounds to be readily obtained, some of which are prepared with great difficulty by the customary methods. These compounds are very useful as pharmaceutical products, as pesticides such as CARBOFURAN, 3,4-dimethylphenyl N-methylcarbamate, ALDICARB, CARBARYL among carbamates, BUTYLATE, EPTC, MOLINATE among thiocarbamates, and CHLORTOLURON and MONURON among ureas, or as intermediates in peptide synthesis such as amino acid carbamates, and there may be mentioned, for example, the synthesis of ASPARTAME (Tetrahedron, volume 39, No. 24, pages 4121 to 4126, 1983, B. Yde et al.).

The invention is illustrated by the examples which follow.

EXAMPLE 1

Preparation of ethyl N,N-di-n-butylcarbamate

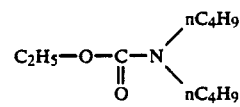

A solution of 26 g (0.2 mole) of di-n-butylamine in 20 ml of anhydrous tetrahydrofuran (THF) is added dropwise to a solution of 15.2 g (0.1 mole) of α-chloroethyl ethyl carbonate

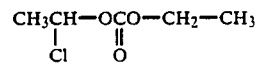

in 80 ml of THF.

The addition is carried out with stirring at 20° C. The reaction is slightly exothermic and the formation of a precipitate of dibutylamine hydrochloride is observed. The mixture is stirred for 2 hours at 20° C., the precipitate removed by filtration and the THF evaporated.

The residue is taken up in 200 ml of dichloromethane, and the solution is washed with 50 ml of aqueous saturated KHCO$_3$ solution and then with 50 ml of water. After the solution is dried over magnesium sulphate, the solvent is removed by evaporation and the residual mixture distilled under reduced pressure.

15.1 g (75% yield) of the expected carbamate are thus obtained.

Boiling point (b.p.) 78°-80° C./40 Pa (0.3 mm Hg).
IR :νC=O: 1700 cm$^{-1}$.

$^1$H NMR: 0.9-1.7 ppm (17H) complex C—CH$_2$—CH$_3$; 3.2 ppm (4H) triplet N—CH$_2$; 4.1 ppm (2H) quartet O—CH$_2$.

EXAMPLE 2

Preparation of ethyl N-n-octylcarbamate

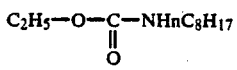

The solution of 7.6 g (0.05 mole) of α-chloroethyl ethyl carbonate in 10 ml of THF cooled to 5°-10° C. is added to a solution, also cooled to 5°-10° C., of 12.9 g (0.1 mole) of n-octylamine in 40 ml of THF.

After the addition has been performed with stirring, the mixture is allowed to return to room temperature and is maintained at this temperature for 2 hours with stirring.

After the precipitate has been removed by filtration and the solvent evaporated, the residue is taken up in 50 ml of ethyl ether, the solution filtered again and the ether phase washed with 50 ml of water.

After the solution is dried over magnesium sulphate, the solvent is removed by evaporation and the residual mixture distilled under reduced pressure.

8.64 g (86% yield) of the expected carbamate are thus obtained.

B.p. 110° C./40 Pa (0.3 mm Hg).
IR: νC=O: 1700 cm$^{-1}$; νN—H: 3300cm$^{-1}$.

$^1$H NMR: 0.1-1.7 ppm (18H) complex (CH$_2$)$_n$CH$_3$; 3.2 ppm (2H) quartet N—CH$_2$. 4.1 ppm (2H) quartet O—CH$_2$. 5.2 ppm (1H) complex

EXAMPLE 3

Preparation of ethyl N-n-octylcarbamate

In a reactor, there are introduced 6.5 g (0.05 mole) of n-octylamine, 30 ml of THF, 10 ml of water and 10 g of potassium carbonate K$_2$CO$_3$. While maintaining the temperature at 5°-10° C., 7.6 g (0.05 mole) of α-chloroethyl ethyl carbonate dissolved in 5 ml of THF are then added dropwise and with stirring.

The mixture is allowed to return to room temperature and is maintained with stirring at this temperature for 1 hour. 50 ml of water saturated with sodium chloride are added, the mixture is extracted with twice 40 ml of ethyl ether, and the ether phases are combined and dried over magnesium sulphate.

After removal of the solvent by evaporation and distillation under reduced pressure, 7.4 g (74%) of the expected carbamate are collected.

B.p. 110°-112° C./40 Pa (0.3 mm Hg).

EXAMPLE 4

Preparation of ethyl N,N-di-n-butylcarbamate

To a solution of 6.5 g (0.05 mole) of di-n-butylamine and 5.56 g (0.055 mole) of triethylamine in 40 ml of THF, 8.4 g (0.055 mole) of α-chloroethyl ethyl carbonate dissolved in 10 ml of THF are added dropwise and with stirring while the temperature is maintained at 5°-10° C.

The mixture is allowed to return to room temperature, and is maintained with stirring at this temperature for 2 hours.

After removal of the precipitate by filtration, evaporation of the solvent and distillation under reduced pressure, 6.3 g (63% yield) of the expected carbamate are collected.

B.p. 76° C./26.6 Pa (0.2 mm Hg).

EXAMPLE 5

Preparation of tert-butyl N-n-octylcarbamate

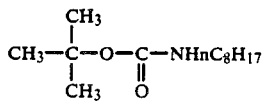

(a) Synthesis of α-chloroethyl tert-butyl carbonate

In a reactor cooled to +5° C., there are introduced 600 ml of dicloromethane, 43.7 g (0.59 mole) of tert-butanol and 94.7 g (0.66 mole) of α-chloroethyl chloroformate. 57 g (0.72 mole) of pyridine are then added dropwise and with stirring while the temperature is maintained at between 10° and 20° C. The mixture is stirred for 4 hours at room temperature.

The reaction mixture is washed with 100 ml of aqueous 1N hydrochloric acid solution, 200 ml of saturated Na$_2$CO$_3$ solution, and with twice 100 ml of iced water. The organic phase is collected and dried over magnesium sulphate.

After evaporation of the solvent and distillation under reduced pressure, 91.5 g (86%) of α-chloroethyl tert-butyl carbonate are obtained.

B.p. 88° C./2.7 kPa (20 mm Hg).
IR: νC=O: 1750 cm$^{-1}$.

$^1$H NMR: 1.5 ppm (9H) (CH$_3$)$_3$—C— singlet; 1.8 ppm (3H) doublet

6.4 ppm (1H) quartet

(b) Reaction of α-chloroethyl tert-butyl carbonate with n-octylamine

A solution of 52 g (0.4 mole) of n-octylamine in 60 ml of anhydrous THF is added dropwise to a solution of 36.2 g (0.2 mole) of α-chloroethyl tert-butyl carbonate in 120 ml of THF. The addition is carried out with stirring at +10° C.

The mixture is stirred for approximately 15 hours at room temperature, the insoluble compounds are removed by filtration and the THF evaporated. The residue is taken up in 400 ml of dichloromethane, and the solution is washed with 100 ml of 1N aqueous HCl solution, 200 ml of water, 100 ml of saturated aqueous KHCO₃ solution and then with 100 ml of water.

After the solution is dried over magnesium sulphate, the solvent is removed by evaporation and the residual mixture distilled under reduced pressure.

36.52 g (80% yield) of the expected carbamate are thus obtained.

B.P. 142° C./200 Pa (1.5 mm Hg).

IR: $\nu C=O$: 1690 cm$^{-1}$; $\nu NH$: 3340 cm$^{-1}$.

¹H NMR: 0.1–1.3 ppm (15H) complex C—(CH₂)n CH₃; 1.4 ppm (9H) singlet (CH₃)₃—C; 3.0 ppm (2H) quartet CH₂—N; 4.7 ppm (1H) complex

(c) Preparation of chloromethyl tert-butyl carbonate

The procedure is as in Example 5 (a). Starting with 7.4 g (0.1 mole) of tert-butanol, 15.48 g of chloromethyl chloroformate and 8.1 ml of pyridine, 9.2 g (55%) of tert-butyl chloromethyl carbonate are obtained.

B.p. 82° C./2 kPa (15 mm Hg).

¹NMR: 1.4 ppm (CH₃)₃—C singlet; 5.8 ppm CH₂—Cl singlet.

IR: $\nu C=O$: 1750 cm$^{-1}$.

(d) Reaction of chloromethyl tert-butyl carbonate with n-octylamine

The procedure is as in 5 (b), but 1-chloroethyl tert-butyl carbonate is replaced by chloromethyl tert-butyl carbonate. Starting with 6.5 g of n-octylamine and 8.5 g of chloromethyl tert-butyl carbonate, 4.3 g (38%) of tert-butyl N-n-octylcarbamate, are obtained identical to that obtained above (5 (b)).

EXAMPLE 6

Preparation of furfuryl N-n-octylcarbamate

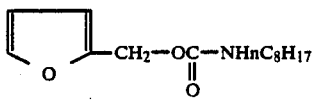

(a) Synthesis of α-chloroethyl furfuryl carbonate

The procedure as in Example 5 (a), but with 0.22 mole of α-chloroethyl chloroformate introduced dropwise into a solution of 0.2 mole of furfuryl alcohol and 0.24 mole of pyridine in 200 ml of dichloromethane.

35.55 g (87% yield) of α-chloroethyl furfuryl carbonate are collected.

B.P. 94°–98° C./13.3 Pa (0.1 mm Hg).

IR: $\nu C=O$: 1750 cm$^{-1}$.

¹H NMR: 1.8 ppm (3H) doublet CH₃—C; 5.2 ppm (2H) singlet CH₂O; 6.3–6.6 ppm (3H) complex H—C= and

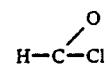

7.5 ppm (1H) complex

(b) Reaction of α-chloroethyl furfuryl carbonate with n-octylamine

The procedure is as in Example 5 (b), but with 10.2 g (0.05 mole) of the above carbonate in 30 ml of THF, and 12.9 g (0.1 mole) of n-octylamine in 15 ml of THF.

11.05 g (87% yield) of the expected carbamate are obtained.

B.p. 162° C./66.6 Pa (0.5 mm Hg), melting pt. (m.p.) 29° C.

IR: $\nu C=O$: 1700 cm$^{-1}$; $\nu NH$: 3340 cm$^{-1}$.

¹H NMR: 0.7 to 1.5 ppm (15H) complex (CH₂)n CH₃ 3.1 ppm (2H) quartet CH₂N 4.9 ppm (1H) broad complex NH 5.0 ppm (2H) singlet CH₂O 6.4 ppm (2H) complex H—C=7.4 ppm (1H) complex

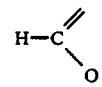

EXAMPLE 7

Preparation of furfuryl N-n-octylcarbamate

In a reactor, there are introduced 6.5 g (0.05 mole) of n-octylamine, 30 ml of THF and 20 ml of 5M aqueous K₂CO₃ solution. With the temperature maintained at 5°–10° C., 11.25 g (0.055 mole) of α-chloroethyl furfuryl carbonate are then introduced dropwise and with stirring.

The mixture is allowed to return to room temperature and is maintained with stirring at this temperature for 18 hours. 50 ml of water saturated with sodium chloride are added, the mixture is extracted with twice 40 ml of ethyl ether and the ether phases are combined and dried over magnesium sulphate.

After removal of the solvent and distillation under reduced pressure, 9.5 g (75%) of the expected carbamate are collected.

B.p. 142° C./26.6 Pa (0.2 mm Hg).

EXAMPLE 8

Preparatioon of benzyl N-n-octylcarbamate

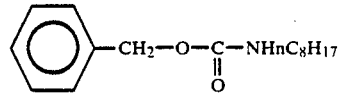

(a) Synthesis of α-chloroethyl benzyl carbonate

The procedure is as in Example 5 (a), but with 200 ml of dichloromethane, 21.6 g (0.2 mole) of benzyl alcohol, 31.6 g (0.22 mole) of α-chloroethyl chloroformate and 0.2 mole of pyridine.

40.5 g (94% yield) of α-chloroethyl benzyl carbonate are thus collected.

B.p. 100° C./66.6 Pa.
IR: $\nu C=O$: 1760 cm$^{-1}$.
$^1$H NMR: 1.8 ppm (3H) doublet CH$_3$—; 5.2 ppm (2H) singlet CH$_2$; 6.4 ppm (1H) quartet O—CH—Cl; 7.3 ppm (5H) singlet aromatic protons.

(b) Reaction of α-chloroethyl benzyl carbonate with n-octylamine

The procedure is as in Example 5 (b), but with 19.4 g (0.15 mole) of n-octylamine in 30 ml of THF and 16.2 g (0.075 mole) of the above carbonate in 40 ml of THF.

17.7 g (90% yield) of the expected carbamate are obtained.

B.p. 180° C./66.6 Pa (0.5 mm Hg).
M.p. 33°-34° C.
IR: $\nu C=O$: 1680 cm$^{-1}$; $\nu NH$: 3380 cm$^{-1}$.
$^1$H NMR: 0.7 to 1.5 ppm (15H) complex (CH$_2$)n CH$_3$ 3.1 ppm (2H) quartet CH$_2$N 4.8 ppm (1H) singlet NH 5.1 ppm (2H) singlet

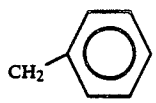

7.3 ppm (5H) singlet aromatic protons

EXAMPLE 9

Preparation of phenyl N-isobutyl carbamate

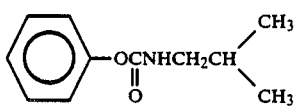

(a) Synthesis of 60-chloroethyl phenyl carbonate

The procedure is as in Example 5 (a), but with 500 ml of dichloromethane, 47 g (0.5 mole) of phenol, 79 g (0.055 mole) of α-chloroethyl chloroformate and 0.5 mole of pyridine.

94.23 g (94%) of α-chloroethyl phenyl carbonate are thus collected.

B.p. 110° C./66.6 Pa (0.5 mm Hg).
IR: $\nu C=O$: 1770 cm$^{-1}$.
$^1$H NMR: 1.7 ppm (3H) doublet CH$_3$; 6.35 ppm (1H) quartet CH—Cl; 7.0 to 7.3 ppm (5H) complex aromatic protons.

(b) Reaction sof α-chloroethyl phenyl carbonate with isobutylamine

The procedure is as in Example 7, but with 7.3 g (0.1 mole) of isobutylamine, 35 ml of 5M aqueous K$_2$CO$_3$ solution and 20.1 g (0.1 mole) of the above carbonate.

After removal of the solvent and recrystallisation in petroleum ether, 12.5 g (65%) of the expected product are obtained.

M.p. 66°-67° C.
IR: $\nu C=O$: 1710 cm$^{-1}$; NH: 3400 cm$^{-1}$.

$^1$H NMR: 0.9 ppm (6H) doublet CH$_3$; 1.8 ppm (1H) multiplet

3.1 ppm (2H) triplet CH$_2$—N; 5.3 ppm (1H) broad singlet NH; 7.0 to 7.3 (5H) complex aromatic protons.

EXAMPLE 10

Preparation of tert-butyloxycarbonylpiperidine

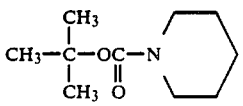

The procedure is as in Example 7, but with 8.5 g (0.1 mole) of piperidine, 60 ml of THF, 20 ml of saturated aqueous K$_2$CO$_3$ solution and 0.11 mole of α-chloroethyl tert-butyl carbonate.

The mixture is stirred for only 2 hours. 14.8 g (80%) of the expected carbamate are collected.

B.p. 96°-98° C./2 kPa (15 mm Hg).
IR: $\nu C=O$: 1690 cm$^{-1}$.
$^1$H NMR: 1.3-1.6 ppm, (15H) —CH$_2$—, CH$_3$—3.3 ppm (4H) CH$_2$N.

EXAMPLE 11

Preparation of S-ethyl N-n-octyl thiocarbamate

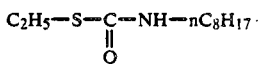

(a) Preparation of α-chloroethyl S-ethylthiocarbonate

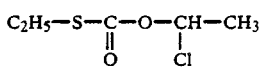

The procedure is as in Example 5 (a), but with 31.5 g (0.22 mole) of α-chloroethyl chloroformate introduced into a solution of 12.4 g (0.2 mole) of ethanethiol and 15.8 g (0.2 mole) of pyridine in 200 ml of dichloromethane.

21.1 g (62.5%) of α-chloroethyl S-ethyl thiocarbonate are obtained.

B.p. 110° C./5.86 kPa (44 mm Hg).
IR: $\nu C=O$: 1720 cm$^{-1}$.
$^1$H NMR: 1.3 ppm triplet CH$_3$; 1.75 ppm doublet CH$_3$; 2.8 ppm quartet CH$_2$—S; 6.5 ppm quartet O—CHCl.

(b) Reaction of α-chloroethyl S-ethyl thiocarbonate with n-octylamine

The procedure is as in Example 7, but with 6.5 g (0.05 mole) of n-octylamine, 30 ml of THF, 20 ml of 5M aqueous K$_2$CO$_3$ solution and 8.43 g (0.05 mole) of the above thiocarbonate.

5.3 g (49%) of the expected thiocarbamate are thus collected.

B.P. 146°-152° C./66.6 Pa (0.5 mm Hg).
IR: $\nu C=O$: 1650 cm$^{-1}$; $\nu NH$: 3300 cm$^{-1}$.

$^1$H NMR: 0.7 to 1.6 ppm (18H) complex (CH$_2$nCH$_3$; 2.8 ppm (2H) quartet CH$_2$S; 3.1 ppm (2H) pseudo-triplet CH$_2$N; 3.2 ppm (1H) broad singlet NH.

EXAMPLES 12 TO 19

Preparation of various benzyl carbamates

In these examples, α-chloroethyl benzyl carbonate is reacted according to the procedure of Example 7 with various primary or secondary amines.

The temperature conditions and reaction time, the physical properties of the products obtained and the yields are shown in Table I.

The procedure is as in Example 11, reacting α-chloroethyl S-ethyl thiocarbonate with hexamethyleneimine.

"MOLINATE" is obtained in a yield of 70% of distilled product.

[B.p. 141° C./1.7 kPa (13 mm Hg)]

EXAMPLE 21

Preparation of tert-butyl N-benzylcarbamate

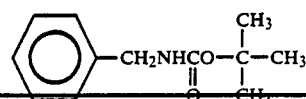

TABLE I

| Ex. no | Amines used | Time | Temperature | Products obtained | Boiling pt. [melting pt.] | Yields of purified products |
|---|---|---|---|---|---|---|
| 12 | C$_6$H$_5$—CH$_2$NH$_2$ | 5 h | 20° C. | C$_6$H$_5$—CH$_2$OC(=O)—NH—CH$_2$—C$_6$H$_5$ | 175° C./13.3 Pa [64° C.] | 84% |
| 13 | C$_6$H$_5$—CH$_2$—NH—CH$_3$ | 4 h | 20° C. | C$_6$H$_5$—CH$_2$OC(=O)—N(CH$_3$)—CH$_2$—C$_6$H$_5$ | 165° C./133.3 Pa | 87% |
| 14 | (C$_2$H$_5$)$_2$NH | 2 h | 20° C. | C$_6$H$_5$—CH$_2$OC(=O)—N(C$_2$H$_5$)$_2$ | 96° C./66.7 Pa | 99% |
| 15 | piperidine (NH) | 2 h | 20° C. | C$_6$H$_5$—CH$_2$OC(=O)—N(piperidinyl) | 126° C./66.7 Pa | 97% |
| 16 | morpholine (O,NH) | 3 h | 20° C. | C$_6$H$_5$—CH$_2$OC(=O)—N(morpholinyl) | 140° C./13.3 Pa | 84% |
| 17 | imidazole | 18 h | 20° C. | C$_6$H$_5$—CH$_2$OC(=O)—N(imidazolyl) | 130° C./133.3 Pa | 50% |
| 18 | NH$_2$—CH$_2$CH$_2$OH | 5 h | 20° C. | C$_6$H$_5$—CH$_2$OC(=O)—NH—CH$_2$CH$_2$OH | 170° C./66.7 Pa | 74% |
| 19 | hexamethyleneimine (NH) | 2 h | 20° C. | C$_6$H$_5$—CH$_2$OC(=O)—N(hexamethyleneiminyl) | 165° C./66.7 Pa | 87% |

EXAMPLE 20

Preparation of S-ethyl N,N-hexamethylenethiocarbamate (MOLINATE)

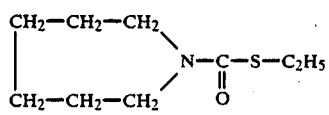

(a) Synthesis of 1,2,2,2-tetrachloroethyl tert-butyl carbonate 9.9 g (0.04 mole) of 1,2,2,2-tetrachloroethyl chloroformate are added in a single portion to a solution of tert-butanol (3 g; 0.04 mole) in dichloromethane (50 ml). The mixture is cooled to 0° C. and 3.2 g (0.04 mole) of pyridine are added dropwise. The mixture is stirred for 4 hours at room temperature. 20 ml of iced water are then added, and the organic phase is separated and washed with 20 ml of iced water. It is dried over magnesium sulphate and the solvent is evaporated. 11.3 g of a white solid (yield: 99%) are obtained, the solid is recrystallised in petroleum ether (87% yield; m.p. 70° C.), and 9.9 g of the purified carbonate are obtained.

B.p. 96° C./866 Pa (6.5 mm Hg).
IR: $\nu C=O$: 1770 cm$^{-1}$.
$^1$H NMR: (CDCl$_3$, TMS): 1.5 (s, CH$_3$) 6.7 (s, CH).

(b) Reaction of the above carbonate with benzylamine 1.1 g (0.01 mole) of benzylamine is dissolved in 20 ml of THF, and 3 ml of 5M aqueous potassium carbonate solution are added.

2.9 g (0.01 mole) of tert-butyl tetrachloroethyl carbonate dissolved in 5 ml of THF are then added at 5° C. The mixture is stirred for 1 hour at 20° C., and the organic phase is decanted and washed with 10 ml of saturated aqueous NaCl solution. The organic phase is dried, the solvent evaporated and the residual mixture distilled: 2.0 g of the expected carbamate are obtained (yield: 96%). B.p. 103° C./6.7 Pa (0.05 mm Hg).

The product is recrystallised in petroleum ether, and 1.84 g of the expected carbamate are obtained (89%). M.p. 54° C. (lit. 53°–54° C.)

EXAMPLE 22

Preparation of tert-butyloxycarbonylimidazole

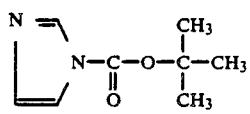

5 g (17.5 mmol) of tert-butyl 1,2,2,2-tetrachloroethyl carbonate dissolved in 10 ml of THF are added at 0° C. to a solution of imidazole (1.2 g; 17.6 mmol) in THF (20 ml) in the presence of 5M aqueous potassium carbonate solution (5 ml). The mixture is stirred for 1 hour at 20° C., and the organic phase is decanted and washed with 10 ml of saturated aqueous NaCl solution.

After the organic phase is dried and the solvents are evaporated, the residue obtained is distilled, and 2.55 g of product are obtained (yield 86%).

B.p. 64° C./133.3 Pa (1 mm Hg).
M.p. 43° C.

EXAMPLE 23

Preparation of 2,3-dihydro-2,2-dimethyl-7-benzofuranyl N-methylcarbamate (CARBOFURAN)

(a) Synthesis of 1-chloroethyl 2,3-dihydro-2,2-dimethyl-7-benzofuranyl carbonate 21.5 g (0.15 mole) of 1-chloroethylchloroformate are added in a single portion to a solution of 2,3-dihydro-2,2-dimethyl-7-benzofuranol (24.6 g; 0.15 mole) in dichloromethane (150 ml). The mixture is cooled to between 0° and 5° C., and 12 g (0.15 mole) of pyridine are added dropwise. The mixture is stirred for 3 hours at 20° C. The organic phase is then washed with 2×50 ml of iced water. It is dried over magnesium sulphate and the solvent is evaporated. A yellow oil is obtained which is distilled. 34.1 g of the expected carbonate is then recovered (84% yield).

B.p. 127° C./66.6 Pa (0.5 mm Hg).

(b) Reaction of the above carbonate with methylamine 5.4 g (0.02 mole) of the above carbonate are dissolved in THF (20 ml). 10 ml of approximately 5M aqueous K$_2$CO$_3$ solution are then added, followed by 1.7 ml (0.02 mole) of a 40% strength solution of methylamine in water. The mixture is stirred for 15 hours at 20° C. The organic phase is decanted and washed with saturated NaCl solution. The solvent is evaporated and the product crystallised in methylcyclohexane. 3.5 g of the desired carbamate are obtained (79% yield).

M.p. 148° C.

(c) The procedure is as in (a) followed by (b), but pyridine is replaced by N,N-dimethylaniline and the intermediate carbonate is not distilled. Starting with 16.4 g of 2,3-dihydro-2,2-dimethyl-7-benzofuranol, 16.8 g (76%) of CARBOFURAN are then obtained, M.p. 147° C.

EXAMPLE 24

Preparation of N-methyl-N'-piperidylurea (a) Synthesis of 1,2,2,2-tetrachloroethyl N-methylcarbamate 34.7 ml (0.4 mmol) of methylamine (in 40% strength aqueous solution) are added dropwise to a solution maintained at 0° C. of 49.4 g (0.2 mole) of 1,2,2,2-tetrachloroethyl chloroformate in dichloromethane (150 ml). The mixture is then stirred for 2 hours at room temperature. The organic phase is washed with 2×100 ml of water and dried over magnesium sulphate.

The product crystallises on evaporation of the solvent, and 42.6 g of the expected carbamate are obtained (88% yield).

M.p. 105°–106° C.
$^1$H NMR: 2.75 (CH$_3$—N); 5.2 (NH); 6.7 (CH—Cl).
IR: $\nu C=O$: 1760 cm$^{-1}$.

(b) Synthesis of N-methyl-N'-piperidylurea 4.83 g (0.02 mole) of the carbamate obtained above are dissolved in 30 ml of THF and 5 ml of water saturated with K$_2$CO$_3$. 1.7 g (0.02 mole) of piperidine is added to this solution maintained at 10° C., and the mixture is stirred for 4 hours at room temperature. The organic phase is decanted and washed with 50 ml of water saturated with NaCl. It is dried over magnesium sulphate, the solvent evaporated and the residue distilled. 1.8 g of the urea is obtained (63% yield).

B.p. 110° C./6.7 Pa (0.05 mm Hg).

EXAMPLE 25

Preparation of imidazolylcarbonylpiperidine

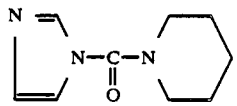

(a) Synthesis of α-chloroethoxycarbonylimidazole 28.6 g (0.2 mole) of chloroethyl chloroformate are added dropwise to a solution of 27.2 g (0.4 mole) of imidazole in 200 ml of dichloromethane cooled in a water bath. The mixture is stirred at room temperature for 4 hours, and 50 ml of iced water are then added. The organic phase is washed with 2×50 ml of water and then dried over magnesium sulphate. After evaporation and distillation, 38.1 g (73%) of α-chloroethoxycarbonylimidazole [B.p. 80° C./66.6 Pa (0.5 mm Hg)] are obtained in the form of a colourless liquid which crystallises spontaneously at room temperature, m.p. 50° C.

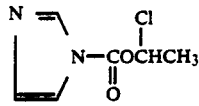

¹H NMR: (60 MHz, CDCl₃, TMS) δ: 1.9 (d, CH₃); 6.7 (q, OCH—Cl); 7.05; 7.4; 8.2 (3 pseudo-singlets, imidazole).
IR: νC=O 1770 cm⁻¹.

(b) Reaction of α-chloroethoxycarbonylimidazole with piperidine

A solution of 8.5 g (0.1 mole) of piperidine in 10 ml of THF is added dropwise to a solution of α-chloroethoxycarbonylimidazole (8.75 g; 0.05 mole) in 50 ml of THF. This solution is cooled to +5° C. while the addition is taking place, and then stirred at room temperature.

The piperidine hydrochloride formed is filtered off and the organic phase then washed once with water. After this is dried over magnesium sulphate and the solvent evaporated, the residual mixture is distilled and 6.2 g (yield: 70%) of the expected product is recovered.
B.p. 134° C./26.6 Pa (0.2 mm Hg).
The liquid obtained crystallises spontaneously in the refrigerator.
M.p. 38° C.
¹H NMR: 1.5 ppm multiplet (CH₂)₃; 3.5 ppm multiplet

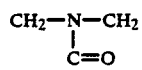

| 7.0 ppm  |   |           |
| 7.15 ppm | } | imidazole |
| 7.8 ppm  |   |           |

IR: νC=O 1690 cm⁻¹.

EXAMPLE 26

Preparation of N,N-diethylimidazolecarboxamide

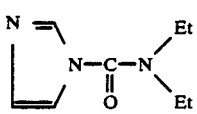

The procedure is as in Example 25 b/, but piperidine is replaced by diethylamine. 6.5 g of the desired urea are obtained (78% yield).
B.p. 106° C./26.6 Pa (0.2 mm Hg).
M.p. 41° C. (Lit. 38°–43° C.).
¹H NMR: 1.2 ppm (t, CH₃); 3.4 ppm (q, CH₂N);

| 7.0 ppm |   |           |
| 7.2 ppm | } | imidazole |
| 7.8 ppm |   |           |

IR: νC=O 1690 cm⁻¹.

EXAMPLE 27

Preparation of 2-methyl-2(methylthio)propanal O-[(methylamino)carbonyl]oxime (ALDICARB)

50 ml of toluene and 6.65 g (0.05 mole) of 2-methyl-2-(methylthio)propanal oxime are added successively to 5 ml of 10N caustic soda. The mixture is stirred for a few moments at room temperature and the water is then removed by azeotropic distillation. The mixture is then cooled in an iced water bath and 7.15 g (0.05 mole) of 1-chloroethyl chloroformate are added dropwise. The mixture is stirred for 1 hour at approximately 10°–15° C. to obtain the 2-methyl-2(methylthio) propanaloxime 1-chloroethylcarbonate. 10 ml (approximately 0.13 mole) of 40% strength aqueous methylamine are then added dropwise, and the mixture is stirred for a further hour at the same temperature. The organic phase is decanted and washed with 10 ml of iced water. The organic phase is dried over magnesium sulphate and evaporated to dryness. 8.7 g of pale brown solid are obtained, m.p. 82–90° C. (70% HP$_{LC}$ pure) which can be further purified either by silica gel chromatography or by chrystallization from isopropylether (63% yield, M.P. 98°–100° C.) HNMR (CDCl₃, 60 MHZ): 1.42 P.P.M/S, 6H) 1.92 (S, 3H) 2.92 (D, 3H) 7.54 (S, 1H).

EXAMPLE 28

Synthesis of tert-butyloxycarbonyl-L-aspartic acid

To a solution of 1.33 g (10 mmol) of L-aspartic acid in a dioxane/water (1:1) mixture (30 ml), 4.2 ml (30 mmol) of triethylamine are added, and the mixture is stirred until solution is complete (approximately 10 min). 2.85 g (10 mmol) of tert-butyl 1,2,2,2-tetrachloroethyl carbonate are then added and the mixture is stirred for 6 hours at 20° C. 50 ml of water are then added and the mixture is extracted with 2×20 ml of ethyl acetate. The aqueous phase is acidified (pH 2–3) with NHCl, and then extracted with 3×30 ml of ethyl acetate. The extract is washed with saturated NaCl solution, dried over MgSO₄ and evaporated. The product obtained is crystallised in ethyl acetate and petroleum ether. 1.4 g (60% yield) of the expected acid is obtained.

M.p. 116–118° C.     m.p.$_{lit.}$ 114–116° C.
       20                    20

[α]$_D$ = −5 (c 1.0 MeOH)   [α]$_D$ lit. = −6.2 (c 1.0 MeOH)

EXAMPLE 29

Preparation of ethyl furfuryloxycarbonyl-glycinate 2.05 g (10 mmol) of α-chloroethyl furfuryl carbonate are added to a solution of 1.03 g (10 mmol) of ethyl glycinate in 6 ml of THF and 4 ml of 0.5M potassium carbonate solution maintained at between 5° and 10° C. The mixture is allowed to come to room temperature and is stirred for 18 hours. 50 ml of water saturated with NaCl are added and the mixture is extracted with 3×40 ml of ethyl ether. The organic phases are combined and dried over magnesium sulphate. After removal of the solvent and distillation, 1.5 g (66% yield) of the expected product is collected.
B.p. 144° C./40 Pa (0.3 mm Hg).
IR: νC=O: 1680 cm¹; νNH: 3280 cm¹.
¹H NMR (CDCl₃, TMS): 1.3 ppm triplet CH₃ 3.95 ppm doublet $$\text{N—CH}_2\text{—}\overset{\overset{\displaystyle O}{\|}}{\text{C}}$$

4.2 ppm quartet $CH_2(CH_3)$ 5.1 ppm singlet $$\text{CH}_2\text{O—}\overset{\overset{\displaystyle \|}{\text{C}}}{\underset{O}{}}\text{—N}$$

5.2 ppm broad singlet NH 6.4 ppm complex H—C= 7.4 ppm complex $$\text{H—C}\overset{\displaystyle /\!\!/}{\underset{\displaystyle}{\text{—O}}}$$

EXAMPLE 30

Preparation of benzyloxycarbonyl-L-proline

To a solution of 1.15 g (10 mmol) of L-proline in 10 ml of methanol and 3 ml of saturated aqueous $K_2CO_3$, 2.36 g (11 mmol) of benzyl α-chloroethyl carbonate are added at 5° C. After 4 hours of reaction, 50 ml of water are added and the mixture is washed with twice 10 ml of ethyl ether. The mixture is acidified to pH 2-3 with 6N HCl and extracted with ethyl acetate.

After evaporation of the solvents and crystallisation in an ethyl acetate/petroleum ether mixture, 2.2 g (88% yield) of Z-(L)-Pro are obtained.

M.p. 75°-76° C. (m.p.$_{Lit.}$ 76°-78° C.).

EXAMPLE 31

Preparation of 1,2,2,2-tetrachloroethyl 2-trimethylsilylethyl carbonate $$(CH_3)_3Si\text{—}CH_2\text{—}CH_2\text{—}O\text{—}\underset{\underset{O}{\|}}{C}\text{—}O\text{—}\underset{\underset{Cl}{|}}{CH}\text{—}CCl_3$$

The procedure is as in Example 21(a). Starting with 5.91 g of trimethylsilylethanol and 12.35 g of tetrachloroethyl chloroformate, 13.6 g (83% yield) of the expected product are obtained.

B.p. 92°-94° C./6.6 Pa.

IR $\nu CO = 1750$ cm$^{-1}$.

$^1$H NMR (CDCl$_3$, external TMS): 0.1 (s, CH$_3$—Si) 1.1(t, CH$_2$—Si) 4.35(t, CH$_2$—O) 6.7(s, CH—Cl)

EXAMPLE 32

Preparation of trimethylsilylethyloxycarbonyl-L-phenylalanine $$(CH_3)Si\text{—}CH_2\text{—}CH_2\text{—}O\text{—}\underset{\underset{O}{\|}}{C}\text{—}NH\text{—}CH\underset{\diagdown CO_2H}{\diagup ^{CH_2\text{—}C_6H_5}}$$

0.83 g of L-phenylalanine (5 mmol) is dissolved in a dioxane/water (1:2) mixture (12 ml) containing 1.4 ml of triethylamine (10 mmol). The mixture is cooled to 0° C. and 1.8 g (5.5 mmol) of the above carbonate dissolved in 4 ml of dioxane is added in a single portion. After 2 hours at 0° C., 20 ml of water are added and the mixture is extracted with twice 20 ml of ether. The aqueous phase is then acidified (pH 2-3) with 6N HCl, and extracted with 3 times 50 ml of ethyl acetate. The extract is dried over MgSO$_4$ and evaporated. 1.4 g (100% yield) of the expected product is obtained in the form of an oil.

$^1$H NMR (CDCl$_3$, TMS) O(s,CH$_3$—Si) 0.9(t, CH$_2$—Si) 3.0(CH$_2$Ph); 4.0(t,O-CH$_2$-C-Si)

$$4.5(m,\underset{\underset{CO_2}{|}}{CH}\text{—N})\ 5.2(s,NH)\ 7.2(s,Ph)\ 8.7(\overset{\overset{O}{\|}}{C}\text{—OH})$$

2 ml of dicyclohexylamine are added to this oil dissolved in 5 ml of ether and, after crystallisation, 1.93 g (78% yield) of dicyclohexylammonium salt is collected, M.p. 111°-112° C.

What is claimed is:

1. A process for preparing carbamic acid derivatives of formula $$\underset{R_2}{\overset{R_1}{\diagdown}}N\text{—}\underset{\underset{O}{\|}}{C}\text{—Y}$$

wherein R$_1$ and R$_2$, are the same or different, and are: hydrogen,
an aliphatic radical having from 1 to 20 carbon atoms,
a cycloaliphatic or araliphatic radical having up to 50 carbon atoms,
or together with the nitrogen atom to which they are attached, form a piperidino, morpholino or imidazolyl ring, said aliphatic, cycloaliphatic, araliphatic radical and said ring being unsubstituted or substituted with acid, alcohol, ester, ether, mercapto or amino groups, and wherein Y is $$OR,\ \text{—SR},\ \text{—N}\underset{\diagdown R_4}{\diagup ^{R_3}}\ or\ \text{—O—N=C}\underset{\diagdown R_7}{\diagup ^{R_6}}$$

group in which:
(i) R denotes:
an aliphatic radical having from 1 to 12 carbon atoms, said radical being unsubstituted or substituted by halogen atoms or with a furyl or trimethylsilyl radical;
a benzyl or nitrobenzyl radical, a phenyl, benzofuranyl or fluorenylmethyl radical, said benzofuranyl radical being unsubstituted or substituted with lower alkyl;
(ii) R$_3$ and R$_4$ are the same or different, and are hydrogen, methyl or together with the nitrogen atom to which they are attached form an imidazolyl ring,
(iii) and R$_6$ and R$_7$, are the same or different and are C$_1$ to C$_{12}$ aliphatic radical or a cycloaliphatic radical with up to 30 carbon atoms, unsubstituted or substituted by lower alkylthio radical or are a hydrogen, a methylthio radical, lower alkyloxy radical, which consists of reacting an amino compound of formula $$HN\underset{\diagdown R_2}{\diagup ^{R_1}}$$

in the presence of an acceptor for hydrohalic acid, at a temperature between $-5°$ C. and $150°$ C., with an alphahalogenated derivative of carbonic acid of formula:

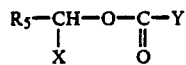

in which $R_1$, $R_2$ and Y are as defined hereinabove, X is a fluorine, chlorine or bromine atom and $R_5$ is an aliphatic radical of 1 to 4 carbon atoms and is unsubstituted or substituted with halogen atoms.

2. The process according to claim 1, wherein X denotes a chlorine atom.

3. The process according to claim 1, wherein the α-halogenated derivative is α-chloroethyl ethyl carbonate, α-chloroethyl tert-butyl carbonate, α-chloroethyl furfuryl carbonate, α-chloroethyl benzyl carbonate, α-chloroethyl phenyl carbonate or α-chloroethyl 2,3-dihydro-2,2-dimethyl-7-benzofuranyl carbonate, 1,2,2,2-tetrachloroethyl tert-butyl carbonate, α-chloroethyl S-ethyl thiocarbonate, α-chloroethoxyimidazole, 1,2,2,2-tetrachloroethyl N-methylcarbamate, 1,2,2,2-tetrachloroethyl 2-trimethylsilylethyl carbonate, or 2-methyl-2-(methylthio)propanal O-[α-chloroethyloxycarbonyl]oxime.

4. The process according to claim 1, wherein
the amine is methylamine, diethylamine, di-n-butylamine, isobutylamine, n-octylamine, ethanolamine, benzylamine, imidazole, hexamethyleneimine, morpholine, diethanolamine, N-methyl-N-benzylamine, piperidine, L-phenylalanine, L-proline, glycine, L-tyrosine, L-serine, L-aspartic acid, ethyl glycinate, phenylglycine or proline.

5. The process according to claim 1, wherein
the reaction is performed in the presence of one or more solvents which are inert with respect to the reagents.

6. The process according to claim 1, wherein the solvent is a member selected from the group consisting of chlorinated aliphatic solvents, cyclic or acyclic ethers, alcohols, acetone, pyridine, acetonitrile and dimethylformamide.

7. The process according to claim 5, wherein
the solvent medium contains water.

8. The process according to claim 1, wherein
the acceptor for acid is an organic or inorganic base.

9. The process according to claim 1, wherein
the acceptor for acid is sodium hydroxide or potassium hydroxide, sodium sulphite, sodium carbonate or bicarbonate or potassium carbonate or bicarbonate, magnesium oxide, a tertiary amine or the starting amine of formula

$R^1$ and $R^2$ having the significance above.

10. The process according to claim 1, wherein the tertiary amine is triethylamine, pyridine or N,N-dimethylaniline.

11. The process according to claim 1 wherein R is tert-butyl, benzyl, para-nitrobenzyl, 9-fluorenylmethyl, 2,2,2-trichloroethyl, trimethylsilylethyl or furfuryl.

12. The process according to claim 1 wherein $R_1$ and $R_2$ are the radical of L-phenylalanine, L-proline, glycine, L-tyrosine, L-serine, L-aspartic acid, proline, ethyl glycinate and phenylglycine.

13. The process according to claim 1, wherein R is an furfuryl, benzyl or phenyl.

14. The process according to claim 1, wherein the α-halogenated derivative is chloromethyl t.butyl carbonate.

* * * * *